United States Patent [19]
Horiguchi

[11] Patent Number: 6,126,444
[45] Date of Patent: Oct. 3, 2000

[54] PLAQUE REMOVER INJECTED WITH WATER OR WITH WATER AND COMPRESSED AIR

[75] Inventor: Shoji Horiguchi, Hachoiji, Japan

[73] Assignee: D&D Corporation, Tokyo, Japan

[21] Appl. No.: 09/098,018

[22] Filed: Jun. 15, 1998

[30] Foreign Application Priority Data

Jul. 22, 1997 [JP] Japan ................................ 9-195437

[51] Int. Cl.[7] ...................................................... A61C 5/00
[52] U.S. Cl. .............................................. 433/216; 514/23
[58] Field of Search .................................. 433/215, 216; 424/48, 49, 54; 514/470, 23, 54, 835, 944

[56] References Cited

U.S. PATENT DOCUMENTS

| | | | |
|---|---|---|---|
| 4,610,872 | 9/1986 | Lynch | 424/49 |
| 4,627,979 | 12/1986 | Lynch | 424/54 |
| 4,627,980 | 12/1986 | Lynch | 424/54 |
| 4,632,937 | 12/1986 | Lynch | 514/470 |
| 5,077,051 | 12/1991 | Gallopo et al. | 424/435 |
| 5,624,906 | 4/1997 | Vermeer | 514/23 |

OTHER PUBLICATIONS

Atkinson, D.R., Cobb, C.M., and Killoy, W.J.: The Effect of an Air–Powder Abrasive System on in Vitro Roof Surfaces. J. Periodontol., Jan., 1984; vol. 55, No. 1, pp. 13–18.

Weaks, L.M., Lescher, N.B., Barnes, C.M., and Holroyd, S.V.: Clinical Evaluation of the Prophy–Jet® as an Instrument for Routine Removal of Tooth Stain and Plaque. J. Periodontol., Aug., 1984: vol. 55, No. 8, pp. 486–488.

Mishkin, D.J., Engler, W.O., Javed, T., Darby, T.D., Cobb, R.L., and Coffman, M.A.: A Clinical Comparison of the Effect on the Gingiva of the Prophy–Jet and the Rubber Cup and Paste Techniques. J. Periodontol., Mar. 1986; vol. 57, No. 3, pp. 151–154.

Galloway, S.E. and Pashley, D.H.: Rate of Removal of Root Structure by the Use of the Prophy–Jet Device. J. Periodontol., Jul. 1987; vol. 58, No. 7, pp. 464–469.

*Primary Examiner*—Nicholas D. Lucchesi
*Attorney, Agent, or Firm*—Jenkins & Gilchrist, A Professional Corporation

[57] ABSTRACT

The invention relates to the improvement of plaque remover consisting of an abradant for removing dental plaque, dirt adhered to teeth, dirt adhered to filler, dirt adhered to prosthesis or dirt adhered to implant by injecting it with water or with water and compressed air. By using granular polysaccharide as the plaque remover derived from natural materials such as cellulose, starch, agar, pulverized particles of a fibrous plant body, particles prepared by decomposing a fibrous plant body, plaque can be removed without damaging not only sound enamel but also dentin prosthesis filler, gingiva and stomal membrane.

9 Claims, 8 Drawing Sheets

PLAQUE REMOVER INJECTED WITH WATER OR WITH WATER AND COMPRESSED AIR

BACKGROUND OF THE INVENTION

The invention relates to a plaque remover which can remove plaque, dirt adhered to teeth and dirt adhered to a denture with ease and reliability.

Since plaque and dirt on teeth cause gingivitis, periodontitis, dental caries and unpleasant halitosis, their removal is significant to keep a mouth clean.

Conventionally, a toothbrush and toothpaste are used daily to remove plaque and dirt from teeth, and they are being improved. But, the toothbrush does not provide a satisfactory cleaning effect to interproximal spaces and tooth-to-gingiva spaces to which the toothbrush is hard to reach.

Generally, plaque, dirt adhered to teeth or dirt adhered to dentures was removed with a toothbrush and toothpaste. But, such a method could not remove plaque thoroughly and required a skilled brushing technique and a long time to remove 70 to 80% of plaque. And, its cleaning efficiency is particularly poor in relation to interproximal spaces and tooth-to-gingiva spaces. Plaque in a periodontal pocket could not be removed with the toothbrush at all, and such plaque could be removed by a dentist only.

Accordingly, there is a device called Water Pik (trade name) developed to remove dirt from teeth by injecting water under pressure. But, a conventional injection method for injecting water only without containing abrasive particles cannot remove plaque thoroughly.

And, there is also a method to inject sodium bicarbonate powder as an abradant together with water and compressed air to remove plaque and dirt from teeth (e.g., AIR-FLOW being sold by SHOFU INC.), and this method is highly effective to remove plaque without damaging gingiva so much as causing any trouble (See cited references "Clinical evaluation of the Prophy-Jet as an instrument for routine removal of tooth stain and plaque. J. Periodontol., 55: 486–488, 1984" by Weaks, L. M., Lescher, N. B., Barnes, C. M. and Holroyd, S. V. and "A clinical comparison of the effect on the gingiva of the Prophy-Jet and the rubber cup and paste techniques. J. Periodontol., 57: 151–154, 1986." by Mishkin, D. J., Engler, W. O., Javed, T., Darby, T. D., Cobb, R. L. and Coffman, M. A.). But, the use of sodium bicarbonate had a disadvantage of damaging good tooth enamel, dentin, and a filler such as a cement and a composite resin (See cited references "The effect of an air-powder abrasive system on in vitro root surfaces. J. Periodontol., 55: 13–18, 1984." by Atkinson, D. R., Cobb, C. M. and Killoy, W. J. and "Rate of the root structure by the use of the Prophy-Jet device. J. Periodontol., 58 : 464–469, 1987." by Galloway, S. E., and Pashley, D. H.). Besides, sodium bicarbonate itself has an unpleasant taste and therefore it is not suitable for use.

Furthermore, such a method had a drawback to grind good tooth enamel and dentin.

Plaque and dirt adhered to a denture is removed mainly with a denture toothbrush, and a foamable cleaning chemical and water are supplementarily injected, but a satisfactory cleaning effect is not expected.

The above-described cleaning with a toothbrush cannot remove plaque thoroughly, and dirt survives in interproximal spaces, tooth-to-gingiva spaces and a recessed portion on a denture without being removed. And, the plaque deposited in such portions causes dental caries, periodontal disease and an odor from dentures.

And, the removal of plaque requires a skilled technique, and it is a troublesome work taking a long time. Especially, it was very difficult for people having a handicapped hand, aged and undergoing orthodontic treatment (since brackets are adhered to teeth and wire is also fixed, plaque is easy to deposit, and cleaning with a toothbrush is difficult).

SUMMARY OF THE INVENTION

Under such circumstances, the inventor has made a devoted study on a method of injecting a plaque remover together with water or water and compressed air. As a result, the inventor has developed a method of removing dental plaque, dirt from teeth, dirt from filler, dirt from prosthesis and dirt from implant by using granular polysaccharide as the plaque remover derived from natural materials such as cellulose, starch, agar, pulverized particles of a fibrous plant body, particles prepared by decomposing a fibrous plant body without damaging not only sound enamel but also sound dentin filler, gingiva and alveolar mucosa. Thus, the present invention was completed.

The invention was achieved based on the above-described knowledge and aims to provide a plaque remover which can remove dental plaque, dirt from teeth, dirt from filler, dirt from prosthesis and dirt from implant safely with ease and reliability.

Another aim of the invention is to provide a plaque remover which can remove plaque, dirt adhered to teeth, dirt adhered to filler, dirt adhered to prosthesis and dirt adhered to implant with more ease and reliability in a short time as compared with a toothbrush.

Another aim of the invention is to provide a plaque remover which is expected to be effective in preventing and treating gingivitis and periodontitis.

Another aim of the invention is to provide a plaque remover which is useful to improve the oral hygiene of persons such as handicapped and aged who could not clean teeth well with a toothbrush.

Another aim of the invention is to provide a plaque remover which is useful to clean prepared cavities and abutments enhancing adhesion of fillings and crowns.

The invention relates to a plaque remover consisting of an abradant for removing dental plaque, dirt adhered to teeth, dirt adhered to filler, dirt adhered to prosthesis or dirt adhered to implant by injecting it with water or with water and compressed air, wherein the abradant consists of granular polysaccharide having a particle diameter of 5 to 300 $\mu$m.

The granular polysaccharide in the invention has a particle diameter of 5 to 300 $\mu$m.

The granular polysaccharide in the invention consists of cellulose or its derivative.

The granular polysaccharide in the invention consists of starch or its derivative.

The granular polysaccharide in the invention consists of agar or its derivative.

The granular polysaccharide in the invention consists of one member or two or more members selected from the group consisting of crystalline cellulose, crystalline cellulose • sodium carmellose, methyl cellulose, ethyl cellulose, hydroxypropyl cellulose, hydroxypropyl methyl cellulose, hydroxypropyl methyl cellulose phthalate, hydroxypropyl methyl cellulose acetate succinate, carmellose, sodium carmellose, calcium carmellose, carboxymethyl ethyl cellulose and cellulose acetate phthalate.

The granular polysaccharide in the invention consists of one member or two or more members selected from the group consisting of wheat starch, rice starch, corn starch, potato starch and hydroxypropyl starch.

The granular polysaccharide in the invention consists of particles prepared by pulverizing a fibrous plant body or decomposing a fibrous plant body and has a particle diameter of 5 to 300 μm.

The fibrous plant body in the invention consists of one member or two or more members selected from the group consisting of a walnut shell, a corncob, an apricot seed shell, a peach seed shell, an almond seed shell, a plum seed shell, a pistachio seed shell and pulp.

In the invention, the granular polysaccharides used are derived from various natural plants, and some of them are classified into food additives and drug additives. They are tasteless and odorless, quite safe for living bodies and used without unpleasant feeling.

These particles have a lower hardness as compared with inorganic abrasive particles. Therefore, they are injected together with water or with water and compressed air to easily remove plaque, dirt adhered to teeth and dirt adhered to dentures. But, they do not grind the tooth enamel, dentin, filler, prosthesis and denture.

And, gingiva and alveolar mucosa are not damaged. When the plaque remover has a particle diameter of less than 5 μm, it does not have the properties of the abrasive particles, and when it exceeds 300 μm, gingiva hurts when the particles are contacted, and the properties of the plaque remover to remove dirt from interproximal spaces and tooth-to-gingiva spaces are degraded. Therefore, the remover of the invention is limited to have a particle diameter of 5 to 300 μm.

Mixing of a disinfectant, an antimicrobial, a scent and the like into the injected granular polysaccharide or water injected together with granular polysaccharide makes it possible to improve sterilizing, antibacterial, deodorizing and refreshing effects.

Granular polysaccharide purified as an abradant having a low hardness, such as crushed particles of cellulose or its derivative, starch or its derivative, agar or its derivative or a fibrous plant body, or particles obtained by decomposing a fibrous plant body, is injected with water or with water and the compressed water to remove plaque, dirt adhered to teeth and dirt adhered to dentures without damaging the tooth enamel, dentin, filler, prosthesis or denture.

DESCRIPTION OF THE PREFERRED EMBODIMENTS

Figure 1:
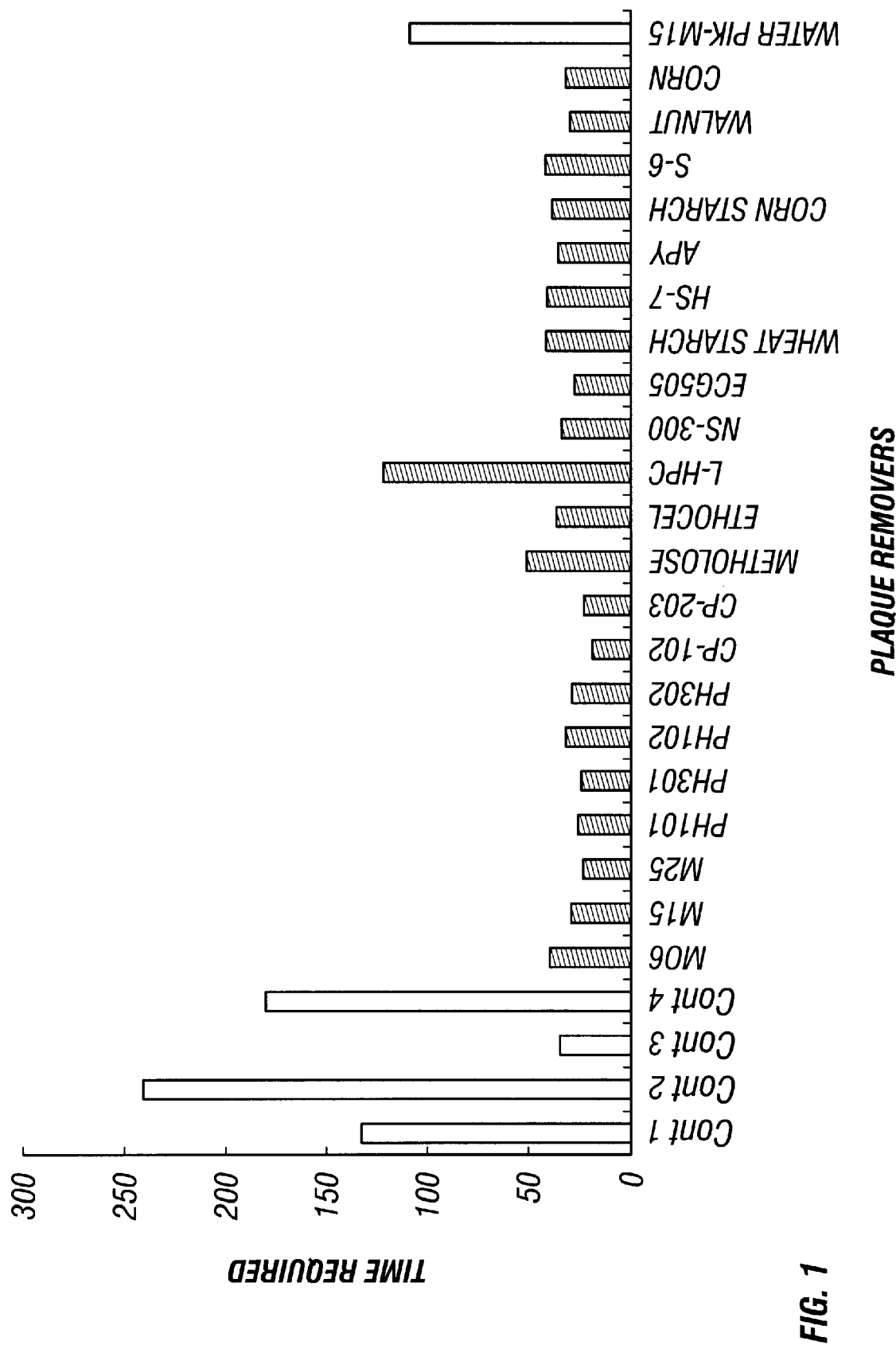
FIG. 1 is a diagram showing the relationship between a plaque remover and a plaque removing time.

Embodiments of the invention will be described with reference to experiments below.

<Experiment 1>

A subject adult who had normal dentition and did not brushed his tooth for 24 hours was laid on a dental chair. Plaque was dyed with a plaque dyeing liquid.

In the respective test groups given below, duration (second) required to thoroughly remove plaque from the front faces of six upper front teeth were compared. Every plaque removal was made by the same dentist(operator).

Time that the operator needed to remove plaque with a toothbrush (without toothpaste) was determined as control 1 (Cont. 1).

Removal of plaque with Water Pik (manufactured by TELEDYNE WATER PIK, Model WP-33J) was determined as control 2 (Cont. 2). Water Pik injects water of 30 ml/minute from a nozzle having a diameter of 1 mm.

Removal of plaque using a tooth cleaner (AIR-FLOW, manufactured by SHOFU INC.) (feeding air pressure of 6 Kg/cm$^2$) with sodium bicarbonate powder was determined as control 3 (Cont. 3).

Removal of plaque using AIR-FLOW ( feeding air pressure of 6 Kg/cm$^2$) without sodium bicarbonate powder (water was injected together with the compressed air) was determined as control 4 (Cont. 4). AIR-FLOW injects water of 38 ml/minute and powder of 0.25 mg/minute.

TABLE 1

| Polysacchraride | | Trade name | Particle diameter | Manufacturer or trading company |
| --- | --- | --- | --- | --- |
| Cellulose or its derivative | Crystalline cellulose | AVICEL M06 | 6(μm) | Asahi Chemical Industry Co., Ltd. |
| Cellulose or its derivative | Crystalline cellulose | AVICEL M15 | 15(μm) | Asahi Chemical Industry Co., Ltd. |
| Cellulose or its derivative | Crystalline cellulose | AVICEL M25 | 25(μm) | Asahi Chemical Industry Co., Ltd. |
| Cellulose or its derivative | Crystalline cellulose | AVICEL PH101 | 50(μm) | Asahi Chemical Industry Co., Ltd. |
| Cellulose or its derivative | Crystalline cellulose | AVICEL PH301 | 50(μm) | Asahi Chemical Industry Co., Ltd. |
| Cellulose or its derivative | Crystalline cellulose | AVICEL PH102 | 120(μm) | Asahi Chemical Industry Co., Ltd. |
| Cellulose or its derivative | Crystalline cellulose | AVICEL PH302 | 120(μm) | Asahi Chemical Industry Co., Ltd. |
| Cellulose or its derivative | Crystalline cellulose | CELPHERE CP-102 | 150(μm) | Asahi Chemical Industry Co., Ltd. |
| Cellulose or its derivative | Crystalline cellulose | CELPHERE CP-203 | 200(μm) | Asahi Chemical Industry Co., Ltd. |
| Cellulose or its derivative | Methyl cellulose | METHOLOSE | * | Shin-Etsu Chemical Co., Ltd. |
| Cellulose or its derivative | Ethyl cellulose | ETHOCEL | * | Shin-Etsu Chemical Co., Ltd. |
| Cellulose or its derivative | Hydroxypropyl cellulose | L-HPC(LH22) | 40(μm) | Shin-Etsu Chemical Co., Ltd. |
| Cellulose or its derivative | Carmellose | NS-300 | * | Gotoku Chemical Co., Ltd. |
| Cellulose or its derivative | Calcium carmellose | ECG505 | * | Gotoku Chemical Co., Ltd. |
| Starch or its derivative | Wheat starch | Wheat starch | 30(μm) | Glico Foods Co., Ltd. |
| Starch or its derivative | Cornstarch | HS-7 | 20(μm) | Japan Corn Starch Co., Ltd. |

TABLE 1-continued

| Polyschraride | | Trade name | Particle diameter | Manufacturer or trading company |
|---|---|---|---|---|
| Starch or its derivative | Cornstarch | APY | 10($\mu$m) | Japan Corn Starch Co., Ltd. |
| Starch or its derivative | Cornstarch | Cornstarch | 20($\mu$m) | Japan Corn Starch Co., Ltd. |
| Agar or its derivative | Agar | S-6 | * | Ina Food Corporation |
| Fibrous plant body | Walnut shell | Walnut | 40($\mu$m) | Sinto Brator Ltd. |
| Fibrous plant body | Corncob | Corn | 40($\mu$m) | Sinto Brator Ltd. |

And, AIR-FLOW has its nozzle made of two-layered pipe that a 1-mm thick inner pipe is covered with a 2-mm thick outer pipe. The powder and air are injected from the inner pipe, while water is injected from the outer pipe.

Test Group 1 removed plaque using AIR-FLOW (feeding air pressure of 6 Kg/cm$^2$) with various types of granular polysaccharides (21 types ranging from M06 to corn shown in Table 1) instead of sodium bicarbonate powder.

Test Group 2 removed plaque using Water Pik with a liquid mixture prepared by stirring 100 ml of water and 2 g of AVICEL M15 shown in Table 1.

A dental vacuum was also used in Conts. 2, 3, 4, and Test Groups 1, 2.

In Table 1, (*) in the particle diameter block indicates that the average particle diameter is not available from the manufacturer.

(Results and consideration)

FIG. 1 shows the results. In FIG. 1, the horizontal axis indicates plaque removers, and the vertical axis indicates time required to remove plaque. It is to be understood that the plaque removers on the horizontal axis of FIG. 1 are given in abbreviation, and their formal names are given in Table 1.

Conts. 1, 2 and 3 are compared. Comparing with a toothbrush, Water Pik and AIR-FLOW with sodium bicarbonate powder have advantages that an interproximal space and a tooth-to-gingiva space can be cleaned better than the toothbrush which is less effective to remove plaque.

But, Water Pik has a disadvantage that it takes a long duration to remove plaque as shown in Cont. 2 of FIG. 1.

AIR-FLOW with sodium bicarbonate powder has a better plaque removing effect than that of the toothbrush as shown in Cont. 3 of FIG. 1.

In view of the plaque removing effect, it is seen from Conts. 1 through 3 that AIR-FLOW with sodium bicarbonate powder is advantageous. But, Experiment 2 shows that AIR-FLOW with sodium bicarbonate powder has a serious disadvantage that its power to abrade the tooth enamel and dentin is high.

Cont. 2 is compared with Cont. 4. It is seen that Cont. 4 injecting water and compressed air has a higher plaque removal ratio as compared with Cont. 2 injecting water only. Injection using water and compressed air seems provided an increased injection velocity higher than when water only is used for injection.

Cont. 3 is compared with Cont 4. It is seen that when sodium bicarbonate powder is injected with water and compressed air, the plaque removing effect is improved remarkably as compared with the injection of water with compressed air. Thus, it is appreciated that a method of injecting the abrasive particles with water and compressed air can remove plaque efficiently.

Conts. 1 and 2 are compared with Test Group 1. It is seen that Test Group 1 removes plaque more effectively than conventional plaque removing methods using a toothbrush and Water Pik. Since water is used in a smaller amount than when Water Pik is used, plaque can be removed by a simple operation.

Cont. 3 is compared with Test Group 1. It is seen that Test Group 1 has the same plaque removing effect as Cont. 3 does. It is also seen that granular polysaccharide has the same effect as sodium bicarbonate powder. But, L-HPC was not suitable since it had high affinity and absorbs water to get gelatinized.

Cont. 2 is compared with Test Group 2. It is seen that injection of abrasive particles, M15, with water can remove plaque effectively as compared with Water Pik which injects water only.

When Cont. 1 is compared with Test Group 2, Test Group 2 had a slightly better plaque removing effect as compared with a conventional toothbrush, because its operation was not easy due to the removal of spattering water. Improvement of its efficiency in future by improving an absorbing device of spattering water can be well predicted. Test Group 2 has a satisfactory utility value in view of its advantage capable of cleaning an interproximal space and a tooth-to-gingiva space which are hard to clean with a toothbrush.

It is seen that as compared with Cont. 1, Test Group 1 can remove plaque in a short duration. A toothbrush has a plaque removing effect limited to where its bristles are contacted. Therefore, the toothbrush is hard to clean an interproximal space and a tooth-to-gingiva space where the toothbrush bristles are hard to reach. And, the toothbrush must be moved finely so as not leave an unbrushed part. In the experiment, even a dentist needed about two minutes to thoroughly remove plaque with the toothbrush.

Meanwhile, Test Group 1 injects granular polysaccharide from the nozzle to spread to enter an interproximal space and a tooth-to-gingiva space, thereby providing a cleaning effect covering a wide range including the portions where the existing toothbrush was hard to clean. Therefore, a skilled brushing technique to finely move the toothbrush bristles is not required. And, the duration needed to remove plaque was decreased.

And, the injected granular polysaccharide also flows into an interproximal space and a tooth-to-gingiva space described above to remove plaque from such spaces. Thus, in addition to the cleaning of the interproximal space which could not be cleaned with the conventional toothbrush alone, tooth-to-gingiva spaces (gingival crevice, a periodontal pocket) which could be cleaned by a dental clinic only could also be cleaned readily.

Test Group 1 did not cause any damage to the tooth enamel, dentin, filler, prosthesis, gingiva and stomal membrane.

L-HPC took substantially the same duration as Cont. 1 because L-HPC itself was adhesive to tooth and required a long duration to remove plaque.

M06, M15, M25, PH301 and PH302 are made of the same material and have average particle diameters 6, 15, 25, 50 and 120 $\mu$m. These crystalline cellulose had very high cleaning capacity.

The operator felt that a larger particle diameter had higher cleaning capacity. But, such large particles remained in the mouth, clogged in interproximal spaces and tooth-to-gingiva spaces and sometimes made it hard to clean to some extent, resulting in taking a little longer cleaning duration.

If a particle diameter is smaller than M25, no unpleasant feeling left in the mouth after removing plaque and rinsing the mouth. But, when PH301 and PH302 were used, sandy feeling remained slightly in the mouth (though not so unpleasant). And, such cellulose having a particle diameter smaller than M25 could be removed easily from the mouth by vacuum.

PH101 and PH102 are made of the same material as PH301 and PH302 and also have substantially the same particle diameter, but their particles have a slightly different and unfixed shape (PH301 and PH302 have a nearly spherical shape). Their cleaning effects were not so different from those of PH301 and PH302 but their power tended to remain in the mouth. And a rather strong unpleasant feeling left in the mouth after rinsing the mouth.

CP-102 and CP203 had a large particle diameter (their average particle diameters are 150 $\mu$m and 200 $\mu$m). Their particles were felt to hurt gingiva (this problem could be remedied when the feeding air pressure to the injection device was adjusted to 4 kg/cm$^2$).

They had a high cleaning effect, and since they had a spherical shape, they could be removed with ease from the mouth by vacuum. Crystalline cellulose shown in Table 1 covering M06 with an average particle diameter of 6 $\mu$m to CP-203 with an average particle diameter of 200 $\mu$m had a plaque removing effect.

METOLOSE, since its particles are soluble in water and has adhesion to teeth, its removal from the mouth was slightly difficult.

ETHOCEL, wheat starch, HS-7, APY, cornstarch and agar were felt having a cleaning capacity slightly lower than crystalline cellulose. But, their cleaning duration was about 40 seconds and had a satisfactory cleaning effect as compared with Cont. 1 and Cont. 2.

NS-300 and ECG505 had a similar cleaning effect to crystalline cellulose. Their particles had a slightly sour taste in the mouth (though not raising a serious problem).

A walnut and corn had a similar cleaning effect to crystalline cellulose.

The removal of plaque (Cont. 2) with Water Pik needed four long minutes to thoroughly remove plaque. It is assumed that Water Pik had a poor result because it was not designed to thoroughly remove plaque.

When Water Pik was used with M15 (Test Group 2), its plaque removing time was shorter than a half of the time needed when Water Pik alone was used.

The cleaning effect was assumed improved by the abrading action of M15.

Test Group 2 did not cause any damage to the tooth enamel, dentin, filler, prosthesis, gingiva and stomal membrane.

Water Pik with M15 was not so effective as compared with Cont. 1, because the treatment was difficult and it took a long duration due to a large volume of spattering water. Improvement of its efficiency in future by improving an absorbing device of spattering water can be well predicted. Its cleaning effect was low as compared with M15 in Test Group 1. It is assumed that the injection of water and M15 together with the compressed air had a higher injection velocity than the injection of water and M15.

As described above, the injection of the plaque remover with water or the injection of water with the compressed air could remove plaque more effectively than using a conventional toothbrush or Water Pik.

<Experiment 2>

Figure 2:
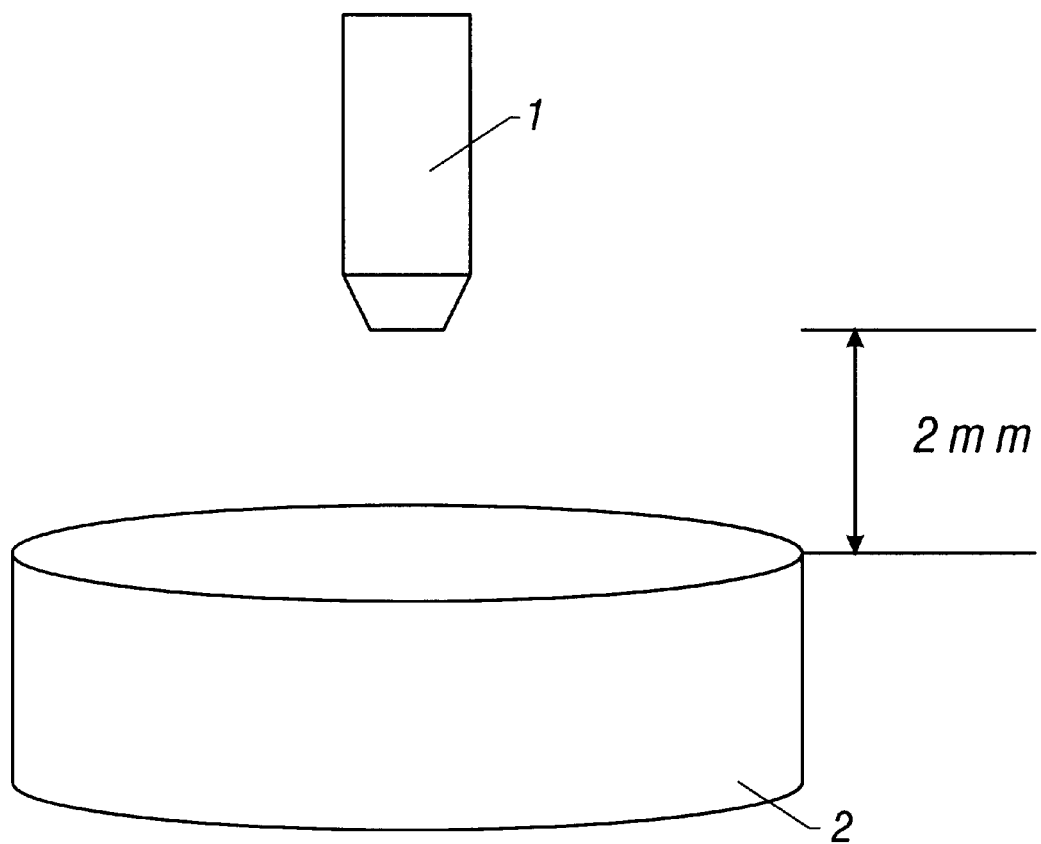
FIG. 2 is an explanatory diagram showing the positions of a nozzle and a sample (tooth enamell, dentin, composite resin) in Experiment 2.

AIR-FLOW with sodium bicarbonate powder and M25 was used to clean a mirror-polished tooth enamel, dentin and a dental composite resin. As shown in FIG. 2, a nozzle 1 had a fixed distance of 2 mm from a sample 2 and injected for 20 seconds. After gold depositing by conventional procedure, SEM pictures were taken.

(Results and Consideration)

The results are shown in FIG. 3 through FIG. 8.

Figure 3:
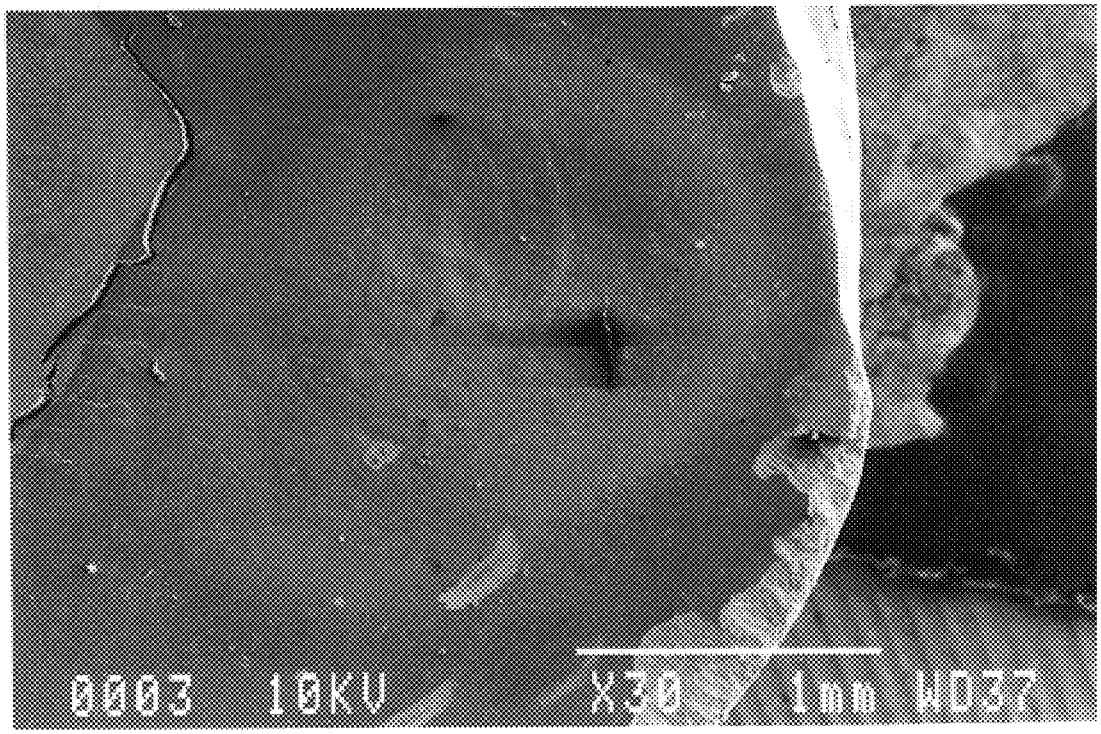
FIG. 3 is an SEM picture of tooth enamel cleaned with sodium bicarbonate power.
Figure 4:
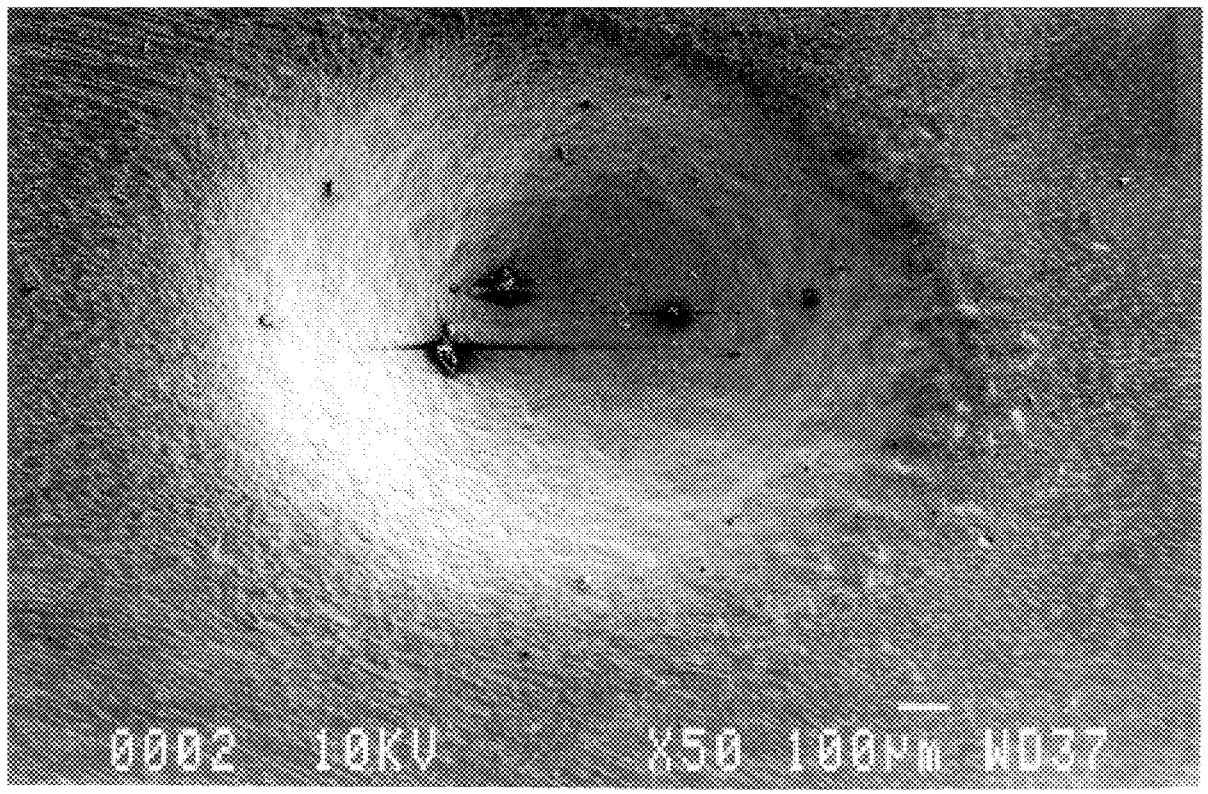
FIG. 4 is an SEM picture of dentin cleaned with sodium bicarbonate powder.
Figure 5:
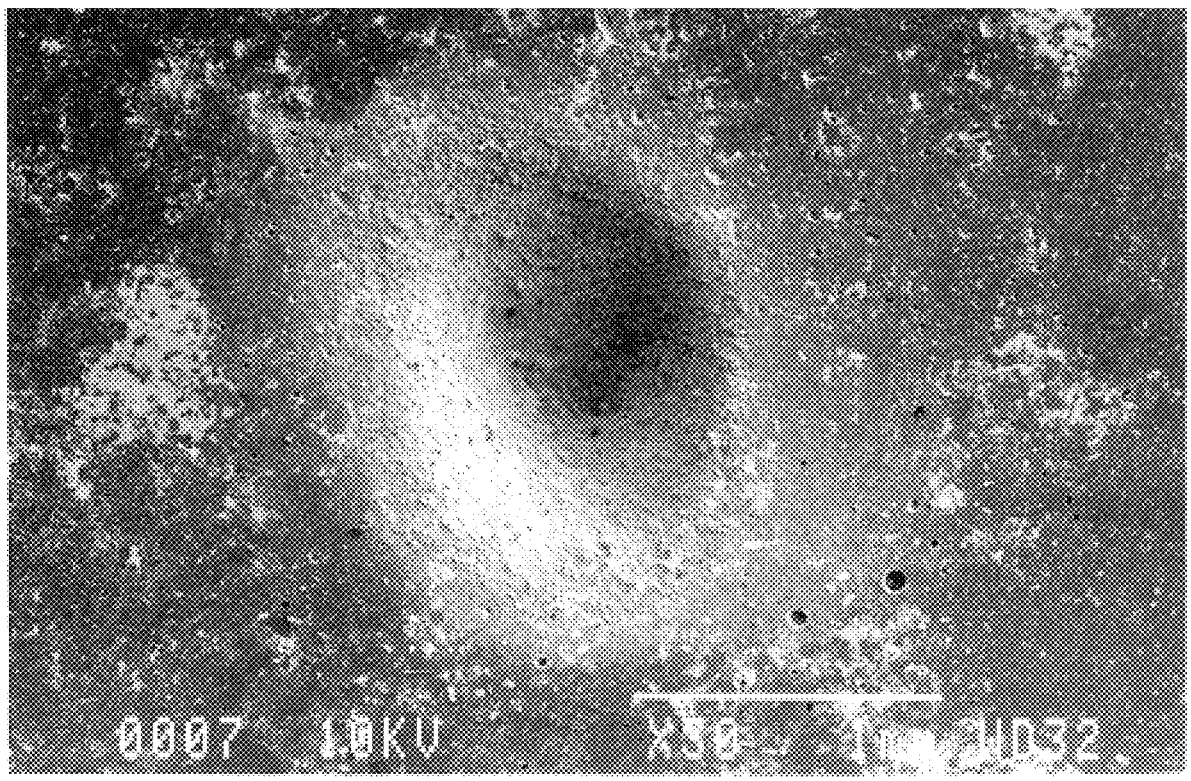
FIG. 5 is an SEM picture of composite resin cleaned with sodium bicarbonate powder.

Injection using sodium bicarbonate powder ground the enamel, dentin and composite resin to form a recess (a circular recess nearly at the center) as shown in FIG. 3 through FIG. 5.

Figure 6:
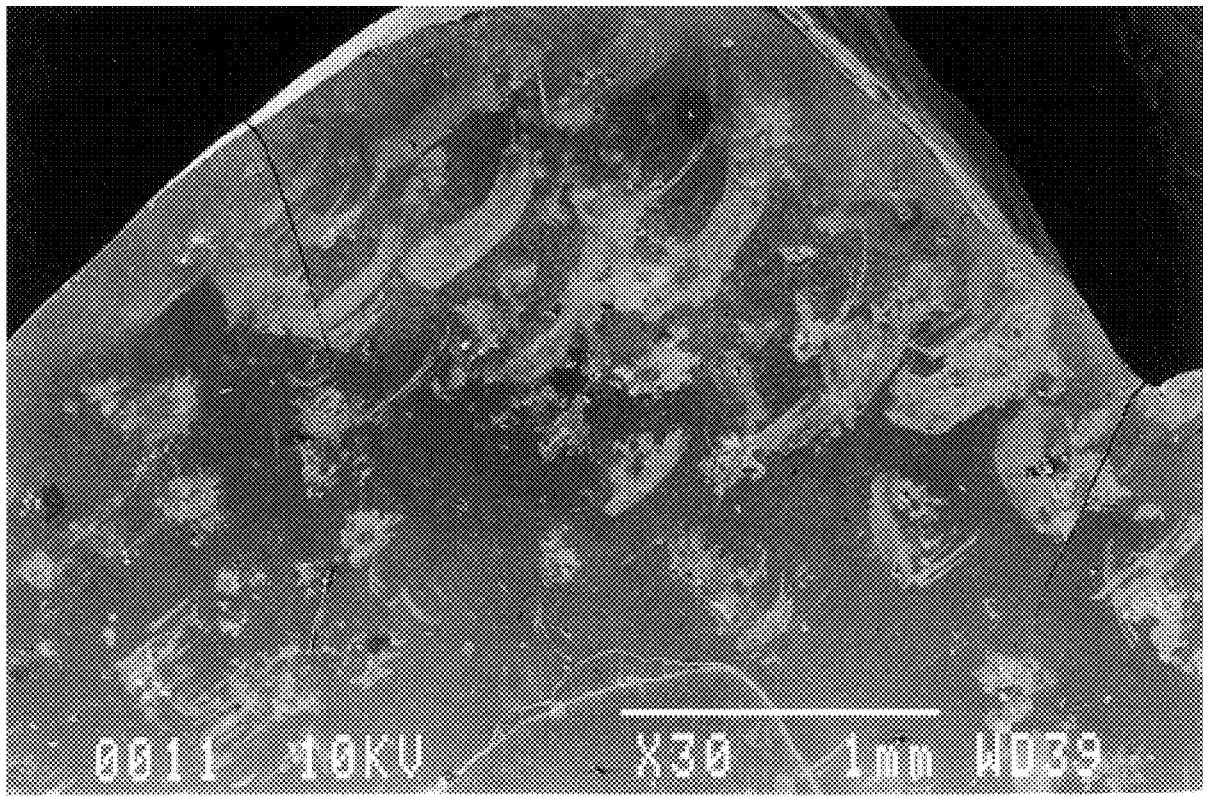
FIG. 6 is an SEM picture of tooth enamel cleaned with M25.
Figure 7:
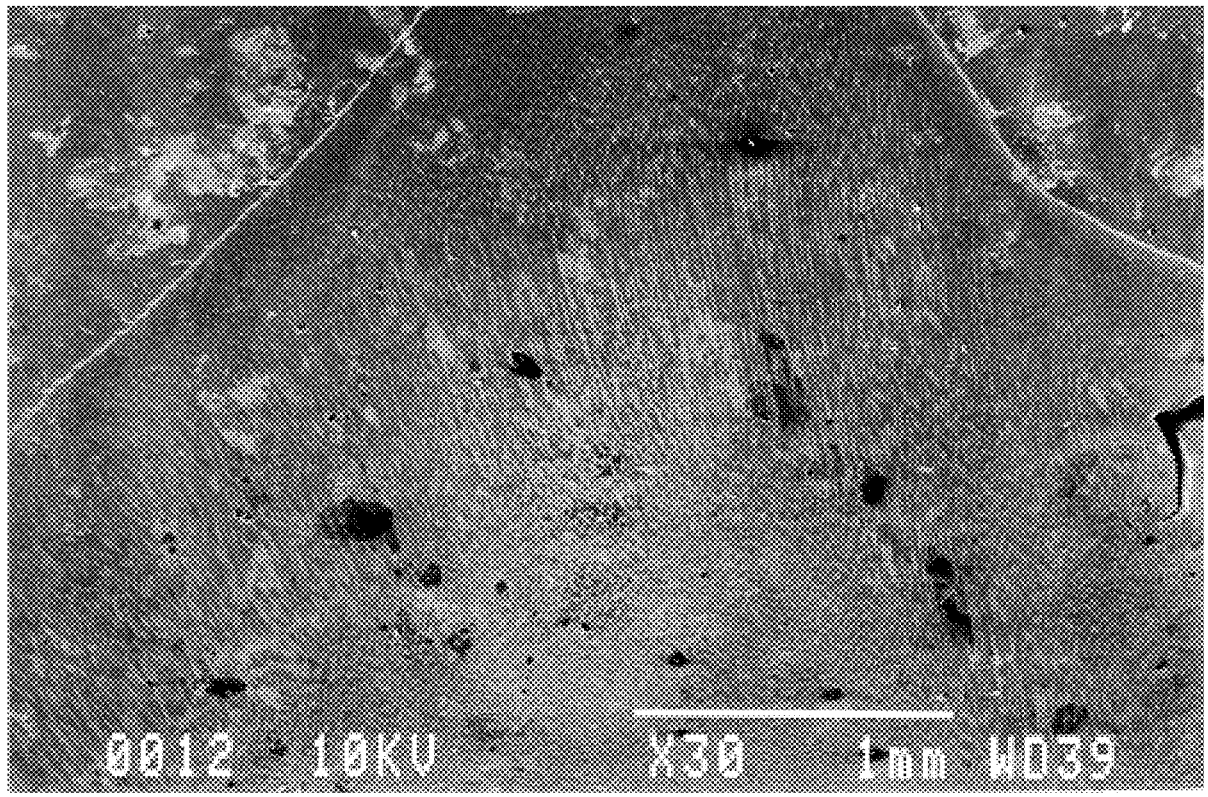
FIG. 7 is an SEM picture of dentin cleaned with M25.
Figure 8:
FIG. 8 is an SEM picture of composite resin cleaned with M25.

When M25 was used, no ground image was observed on the tooth enamel and dentin as shown in FIG. 6 and FIG. 7. As shown in FIG. 8, a ground impression (a circular recess nearly at the center) was very slightly observed on the composite resin. This ground impression is of a level formed when a toothbrush is used with toothpaste and does not cause any problem.

It is apparent from the above description that a damage to teeth by the injection of granular polysaccharide is smaller than sodium bicarbonate powder is used.

<Experiment 3>

A duration for thorough cleaning to remove dirt was compared by cleaning dentures (not cleaned for two days) used for first and second molars on the lower jaw after cleaning with a denture toothbrush as the conventional method and with AIR-FLOW with M25, ground walnut shell powder (an average particle diameter of 60 $\mu$m) and ground corncob powder (an average particle diameter of 60 $\mu$m).

Dirt on the dentures was dyed with a plaque dyeing liquid.

(Results and Consideration)

The denture toothbrush took 250 seconds to remove the dirt thoroughly. AIR-FLOW used with M25, the walnut shell powder and the corncob powder took 40 seconds, 30 seconds and 35 seconds respectively to complete the cleaning. M25, the walnut shell powder and the corncob powder did not damage the denture surface. The denture toothbrush was hard to remove plaque adhered into small recesses formed on the denture. But, AIR-FLOW used with M25, the walnut shell powder and the corncob powder could remove plaque from such recesses with ease and made the cleaning time short.

<Experiment 4>

A subject adult now undergoing orthodontic treatment who did not clean the teeth for 24 hours was laid on a dental chair. And, plaque on the teeth was dyed with a plaque dyeing liquid.

The front faces of six upper front teeth were cleaned to remove plaque with a conventional toothbrush and AIR-FLOW with granular polysaccharide M25 shown in Table 1 for five minutes, and the cleaned states were compared.

(Results and Consideration)

The cleaning with the toothbrush resulted in leaving a large amount of plaque in interproximal spaces, tooth-to-gingiva spaces and tooth-to-wire spaces. On the other hand, AIR-FLOW used with M25 removed plaque thoroughly from such portions.

A person undergoing orthodontic treatment for straightening teeth and having brackets and wire has recessed portions where the toothbrush bristles cannot reach easily as compared with a person not undergoing such treatment. But, M25 injected by AIR-FLOW could easily reach such recessed portions to remove plaque from there.

What is claimed is:

1. A plaque remover injected with water or with water and compressed air comprising an abradant for removing dental plaque, dirt adhered to teeth, dirt adhered to filler, dirt adhered to prosthesis, or dirt adhered to an implant injected with water or with water and compressed air, wherein the abradant comprises primarily a granular polysaccharide.

2. The plaque remover injected with water or with water and compressed air according to claim 1, wherein the granular polysaccharide has a particle diameter of 5 to 300 µm.

3. The plaque remover injected with water or with water and compressed air according to claim 1, wherein the granular polysaccharide comprises a cellulose or a cellulose derivative.

4. The plaque remover injected with water or with water and compressed air according to claim 3, wherein the granular polysaccharide consisting of at least one member selected from the group consisting of crystalline cellulose, crystalline cellulose-sodium carmellose, methyl cellulose, ethyl cellulose, hydroxypropyl cellulose, hydroxypropyl methyl cellulose, hydroxypropyl methyl cellulose phthalate, hydroxypropyl methyl cellulose acetate succinate, carmellose, sodium carmellose, calcium carmellose, carboxymethyl ethyl cellulose and cellulose acetate phthalate.

5. The plaque remover injected with water or with water and compressed air according to claim 1, wherein the granular polysaccharide comprises a starch or a starch derivative.

6. The plaque remover injected with water or with water and compressed air according to claim 5, wherein the granular polysaccharide consisting of at least one member selected from the group consisting of wheat starch, rice starch, corn starch, potato starch and hydroxypropyl starch.

7. The plaque remover injected with water or with water and compressed air according to claim 1, wherein the granular polysaccharide comprises an agar or an agar derivative.

8. The plaque remover injected with water or with water and compressed air according to claim 1, wherein the granular polysaccharide comprises particles prepared by pulverizing a fibrous plant body or decomposing a fibrous plant body and has a particle diameter of 5 to 300 µm.

9. The plaque remover injected with water or with water and compressed air according to claim 8, wherein the fibrous plant body consisting of at least one member selected from the group consisting of a walnut shell, a corncob, an apricot seed shell, a peach seed shell, an almond seed shell, a plum seed shell, a pistachio seed shell and pulp.

* * * * *

UNITED STATES PATENT AND TRADEMARK OFFICE
CERTIFICATE OF CORRECTION

PATENT NO. : 6,126,444
DATED : October 3, 2000
INVENTOR(S) : Shoji Horiguchi

It is certified that error appears in the above-indentified patent and that said Letters Patent is hereby corrected as shown below:

On the title page:

under "*Attorney, Agent, or Firm*," delete "Jenkins" and insert --Jenkens--.

Column 7, line 15, delete "power" and insert --powder--.

Signed and Sealed this

Sixth Day of March, 2001

*Attest:*

NICHOLAS P. GODICI

*Attesting Officer*     *Acting Director of the United States Patent and Trademark Office*